United States Patent [19]
Rossini et al.

[11] Patent Number: 5,312,387
[45] Date of Patent: May 17, 1994

[54] ROUNDED CORNER FASTENING TAB DIAPER CLOSURE

[75] Inventors: Steven J. Rossini, Hugo; Roland R. Midgley, Minneapolis, both of Minn.

[73] Assignee: Minnesota Mining and Manufacturing Company, St. Paul, Minn.

[21] Appl. No.: 16,744

[22] Filed: Feb. 11, 1993

[51] Int. Cl.⁵ ............................................. A61F 13/15
[52] U.S. Cl. ..................................... 604/389; 604/391
[58] Field of Search ............... 604/358, 389, 390, 391, 604/385.1; 128/849; 24/DIG. 11

[56] References Cited

U.S. PATENT DOCUMENTS

| | | | |
|---|---|---|---|
| 3,848,594 | 11/1974 | Buell. | |
| 5,085,655 | 2/1992 | Mann et al. | 604/389 |
| 5,154,715 | 10/1992 | Van Iten | 604/389 |
| 5,176,670 | 1/1993 | Roessler et al. | 604/389 |

FOREIGN PATENT DOCUMENTS

| | | | |
|---|---|---|---|
| 0379850 | 8/1990 | European Pat. Off. | B31D 1/02 |
| 2185383 | 9/1987 | United Kingdom | A41B 13/02 |
| 2206506 | 11/1989 | United Kingdom | A41B 13/02 |

Primary Examiner—Randall L. Green
Assistant Examiner—Rob Clarke
Attorney, Agent, or Firm—Gary L. Griswold; Walter N. Kirn; William J. Bond

[57] ABSTRACT

A fastening tab for a disposable diaper having a free end having a distal half with a maximum width X-V and a proximal half minimum width y, where x is the width of the manufacturer's end. The tape provides a maximum peel front at the distal end of the attached fastening tab providing a more secure closure and is capable of being cut from a stock roll in a repeating pattern without any waste.

13 Claims, 2 Drawing Sheets

ROUNDED CORNER FASTENING TAB DIAPER CLOSURE

BACKGROUND AND FIELD OF THE INVENTION

The invention concerns a fastening tab for a diaper, or the like, particularly, a pressure-sensitive adhesive diaper fastening tape or mechanical fastener element.

Most conventional diaper fastening tabs are pressure-sensitive adhesive tapes or mechanical fastening elements that are rectangular in shape. This regular shape has the advantage in that it is easily converted (e.g., cut) from a stock roll or web into the individual fastening tabs and attached to the diaper, for example, as described in U.S. Pat. No. 3,848,594. However, this design is limited in terms of the fastening characteristics obtainable with a given pressure-sensitive adhesive or mechanical fastener hook and loop structure.

An alternative fastening tab design to the conventional rectangular shape is described in UK Patent Application No. 2 185 383 A. In this patent, the free end (the end attached by the user) of the diaper fastening tab tapers from its outermost peripheral end to its base, where the width is approximately that of the manufacturer's bond end of the fastening tab. A problem with this type of construction or design is that the distal end of the user-applied free end of the fastening tab can be removed at relatively low peel forces, making the tab more easily removable by the infant and increasing the potential for tab failure.

A fastening tab structure incorporating features of the rectangular tab and that of UK Patent Application No. 2 185 383 A is described in European Patent Application No. 379 850. In this patent application, the distal end of the diaper fastening tape free end is generally free of adhesive in the small portion of the free end which tapers. The remaining user applied free end portion of the diaper fastening tape has a conventional rectangular shape. The advantage of the tapered adhesive-free distal end, of the fastening tape free end, is the elimination of sharp corners that children might accidentally cut themselves upon. The performance of the tape described in this patent would not be substantially different from that of conventional fastening tapes. Significant waste product would be created in the manufacture of these diaper tape tabs from a standard adhesive-coated stock roll or web.

An approach similar to that in European Patent Application No. 379 850 is described in UK Patent Application No. 2 206 506 A. A rounded end is similarly provided to protect against irritation from sharp corners to either the parent or the baby. This design would likewise have the limitations of European Patent Application No. 379 850.

There continues to be a need for improved diaper fastening tab designs from the prospective of performance, manufacturability and cost. The invention is directed at providing a novel fastening tab design which is advantageous in terms of all these perspectives. Particularly, the novel fastening tabs can be readily cut from a stock roll without creation of waste and provide fastening tabs with improved peel performance relative to conventional tab designs.

SUMMARY OF THE INVENTION

In accordance with the invention, a diaper fastening tab is provided having a rectangular manufacturer's bond end of a width x and a free end divided into a distal half and a proximal half, the proximal half having a minimum width of y, and the distal half having a maximum width x-y, where x-y is greater than y. The distal half has a shape such that the side edge of the distal half is an inverted mirror image of the proximal half side edge, allowing the fastening tab to be continuously cut as a repeating pattern from a single roll of stock material with little or no waste product.

The invention tab design also provides increased peel resistance at the distal end of the tab, decreasing the potential for pop off or inadvertent removal. The overall tab design provides novel fastening tab free end shapes with improved peel performance over comparable rectangular conventional tab free ends, with the same cross-sectional attachment area at their respective free ends.

DETAILED DESCRIPTION OF THE INVENTION

Figure 1:
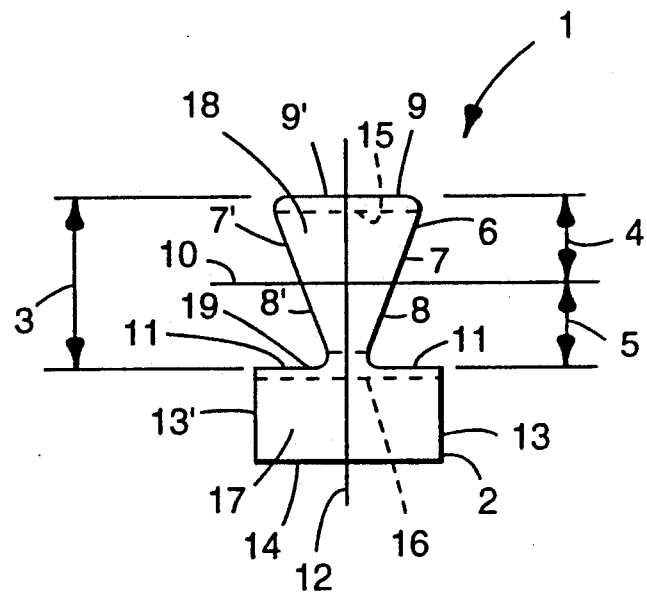
FIG. 1 is a plan view of a fastening tab of the present invention.
Figure 3:
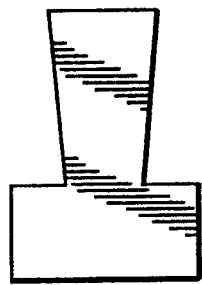
FIGS. 3–7 are alternative fastening tab designs shown in plan view.
Figure 4:
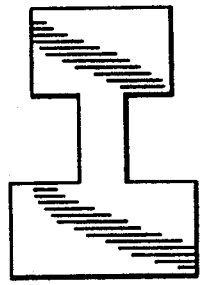
Figure 5:
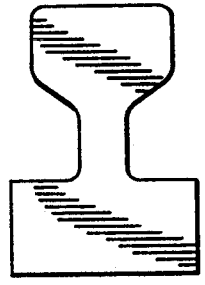

A diaper fastening tab of the invention 1 is shown in FIG. 1. The fastening tab is divided into a manufacturer's bond end 2 and a free end 3. The manufacturer's bond end 2 is attached to a diaper (not shown) side edge by conventional means, such as a pressure-sensitive adhesive, a hot-melt adhesive, sonic bonding, or the like. The free end 3 is provided with a fastening surface 18 which will adhere to a suitable surface on the front or frontal portion of the diaper (not shown). The fastening surface 18 on the free end 3 can be created by a suitably formulated pressure-sensitive adhesive, a mechanical fastener, or a cohesive adhesive.

The free end 3 of the fastening tab 1 is divided into a distal half 4 and a proximal half 5, where the bottom edge of the proximal half 5 is the upper-most edge 19 defined by the largest true rectangle or parallelagram included within the manufacturer's bond end 2.

The distal half 4 and proximal half 5 of the free end 3 are separated by an imaginary transverse line 10. The distal half side edge (7,7') and proximal half side edge (8,8') are inverted mirror images of each other taking the transverse line 10 which separates the two halves (4 and 5) as the plane of reflection. Using this same plane of reflection as a reference, the distal half 4 top edge (9,9') is a composite of two mirror images (9,9') on either side of the bisecting longitudinal center line 12. Side edges 7 and 8 are mirror images of side edges 7' and 8'.

Figure 6:
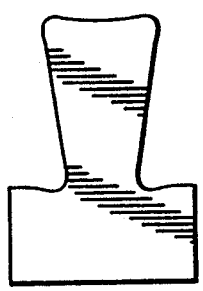
Figure 7:
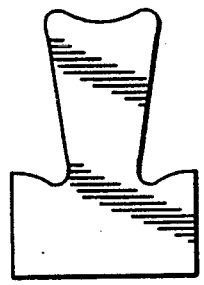

The manufacturer's bond end 2 is preferably a rectangular structure as shown in FIG. 1, however, other shapes, such as that shown in FIGS. 6 and 7 are also possible. The side edges (13,13') of the manufacturer's bond end are mirror images of each other and preferably parallel lines at right angles to the manufacturer's end bottom edge 14, forming an imaginary included rectangle having a top edge 19. Edge segments 11 are mirror images of each other.

In a preferred arrangement, as shown in FIG. 1, the distal half 4 of the free end 3 is provided with an adhesive-free, or other fastener-free, surface, 15 or 16, provided to facilitate grasping of the fastening tab free end 3 by the user. A corresponding fastening surface free zone, 16 or 15, is provided at the base of the proximal half, which can serve as a bonding surface, such as for a y bond as described in U.S. Pat. No. 3,848,594.

Figure 2:
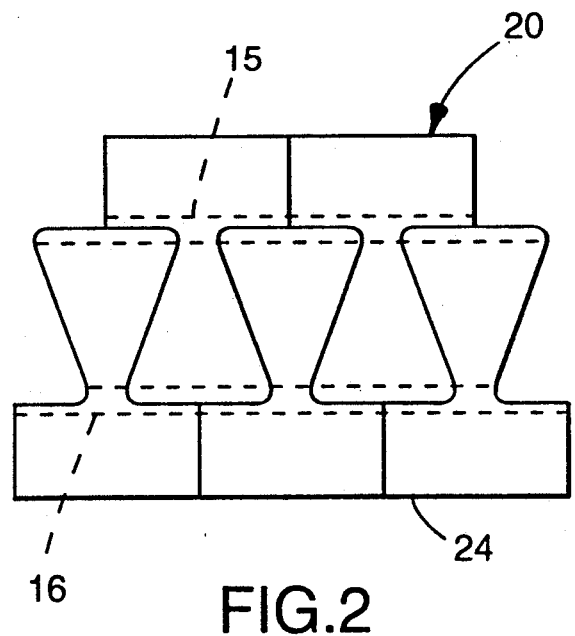
FIG. 2 is a fragmentary plan view showing the pattern from which the fastening tab of FIG. I is cut from a roll of stock material.

The overall design of the fastening tab described in reference to FIG. 1 permits easy cutting, e.g., die cutting, of multiple fastening tabs from a stock roll 20 of fastener material, as shown in FIG. 2. The structure of the side edge 24 of this stock material would provide the structure of the manufacturer's end bottom surface 14.

The description of the overall structure of the FIG. 1 fastening tab applies equally to the structures depicted in FIGS. 3–7. The same structural relations discussed above are also present in the FIGS. 3–7 designs, which also permit these fastening tabs to be continuously cut in a repeating pattern from a stock roll 20 with little or no waste, while providing improved peel performance at the fastening tab free end.

The free end fastening surface 18 is provided by any suitable conventional fastening material such as a mechanical fastener hook or loop region. If the free end fastening surface 18 is a pressure-sensitive adhesive, the frontal portion of the diaper is preferably reinforced in some known manner to prevent tearing thereof when the free end 3 is removed from the diaper frontal portion. If the fastening surface 18 is a hook or loop-type material, the corresponding surface on the front of the diaper must be formed from a matching hook or loop material. Any matching hook and/or loop-type material would be suitable. Similarly, with a cohesive adhesive on the fastening surface 18, the frontal portion of the diaper would have to be provided with a mating cohesive adhesive surface.

Pressure-sensitive or cohesive adhesives can be solvent coated or hot-melt coated onto a backing such as a film, nonwoven web, paper, coated paper or a woven fabric. The same, or different, pressure-sensitive adhesives can be used on the manufacturer's end fastening surface 17 and the fastening surface 18 with optional adhesive free zones, 16 or 15, separating the two adhesive-coated zones (17 and 18). Mechanical fastener elements can be formed directly on a fastening tab stock roll backing or applied as a separate element to the stock roll backing by suitable conventional bonding methods.

The manufacturer's end 2 has a width x. The proximal half 5 of the free end 3 has a minimum width of y providing the distal half 4 of the free end with a maximum width x-y, which is larger than Y. This relationship provides a fastening tab free end with a maximum peel force at the distal half 4 of the free end 3 creating a more secure bond to the diaper front outer face when compared to a conventional fastening tab with similar surface area. Preferably, the maximum width xy of the distal half 4 is closely adjacent, or adjacent, the fastening surface free zone (15 or 16) or the free end top edge (9,9') so as to provide the peel maximum close to, or at, the initial peel propagation front. With preferred embodiments, the distal half 4 maximum width x-y is at least 1.2 times Y, more preferably 2 times y, and most preferably 4 times y, with y being at least about 1 cm. This provides increased peel force maximums at the distal half of the free end, as compared to identical surface area conventional rectangular fastening tab designs.

Compared to conventional rectangular fastening tab free ends of equivalent cross-sectional area, the fastening tab free ends of the invention provide improved peel force resistance at the distal half 4 of the fastening tab free end 4, minimizing the potential for inadvertent fastening tab removal or fastening tab pop off. Once the initial peel force maximum is overcome by the parent, the remaining portion of the fastening tab can be opened at forces at, or below, those of a conventional rectangular fastening tab of equivalent free end surface area.

The manufacturer's bond end is generally half as long and twice as wide as conventional manufacturer's bond ends of similar cross-sectional area for rectangular fastening tapes. This provides higher peel force resistance, reducing the tendency for peel mode failure.

The entire invention fastening tab can be continuously die cut in a repeating pattern from a conventional web or stock roll with essentially no waste product, which is advantageous in terms of cost, manufacturability (it is difficult to remove small die cut waste pieces cut from a rapidly moving web) and environmental concerns.

The following examples are submitted to demonstrate the presently contemplated best mode and further preferred embodiments of the invention and are not intended to be limiting thereof.

EXAMPLES

Examples 1 and 2 and Comparative Examples 1–2

The example tapes 1 and 2 describe fastening tabs with trapezoidal-shaped free ends coated with two different tackified synthetic rubber (block copolymer of polystyrene and polyisoprene) adhesives (A and B, respectively). Comparative example tapes 1 and 2 had a rectangular shape, coated with the same adhesives and of the same surface area on their free ends as Example tapes 1 and 2, respectively. The example 1 tape was formed using a backing of 4.0 mil (102μ) matte polypropylene film. The example 2 tape backing was a 6.0 mil (152μ) brown Kraft paper. Both adhesives (A and B) were coated onto the backings out of solvent and comprised Kraton ™ 1107 tackified with Wingtack ™ Plus and Wingtack ™ 10. All the tapes (1 inch, 2.54 cm wide samples) were tested for 90 degree initial peel performance against a 1.4 mil (35.6μ) embossed polyethylene film using ASTM 3125. The film was adhered to a panel by a double-coated tape rolled down with two passes of a 4.5 pound roller. The tapes were also tested for 135 degree peel (using ASTM 3120) against the same polyethylene film. The tape samples were again 1 inch wide, and the film similarly secured to the panel. The results are set forth in Table I.

TABLE I

| Tape Ex. | Free End Zone | X | Y | X − Y | $\frac{X-Y}{Y}$ | 90 Degree Peel | 135 Degree |
|---|---|---|---|---|---|---|---|
| 1 | 7.87 cm² | 4.13 cm | 1.59 cm | 2.54 cm | 1.59 | 1405 gm | 1620 gm |
| 2 | 9.98 cm² | 5.72 cm | 1.91 cm | 3.81 cm | 2 | 1185 gm | 1330 gm |

TABLE I-continued

| Tape Ex. | Free End Zone | X | Y | X − Y | $\frac{X-Y}{Y}$ | 90 Degree Peel | 135 Degree |
|---|---|---|---|---|---|---|---|
| C1 | 7.87 cm² | N/A | 2.06 cm | 2.06 cm | 1 | 1150 gm | 1325 gm |
| C2 | 9.98 cm² | N/A | 3.18 cm | 3.18 cm | 1 | 965 gm | 1235 gm |

For both these tapes, the 90 degree peel performance was about 19 percent higher for the invention tape constructions. The 135 degree peels were also significantly higher for the invention tape constructions.

EXAMPLE 3 AND COMPARATIVE EXAMPLE 3

The fastening tapes described in this Example and Comparative Example were coated with a similar synthetic rubber-based pressure-sensitive adhesive and tested for T-peel against a release coated (urethane low-adhesion backsize) ethylene/propylene copolymer tape. The shapes were, again, trapezoidal and rectangular, respectively. The T-peel was a variation of ASTM D1876-72, using an Instron- head speed of 12 in/min (30.5 cm/min), and the average of four initial peel values of the free ends reported in Table II. The results are set forth in Table II.

TABLE II

| Tape Ex. | Free End Area | X | Y | X − Y | $\frac{X-Y}{Y}$ | T-Peel |
|---|---|---|---|---|---|---|
| 3 | 7.87 cm² | 5.1 cm | 1.59 cm | 3.51 cm | 2.2 | 940 gm |
| C3 | 7.87 cm² | N/A | 2.06 cm | 2.06 cm | 1 | 490 gm |

The various modifications and alterations of this invention will be apparent to those skilled in the art without departing from the scope and spirit of this invention, and this invention should not be restricted to that set forth herein for illustrative purposes.

We claim:

1. A diaper fastening tab comprised of a rectangular manufacturer's bond end and a free end having a fastening surface, the manufacturer's bond end having a width x wherein the improvement comprises a free end formed into a distal half and a proximal half, adjacent the manufacturer's bond end, the proximal half having a minimum width y, and the distal half having a maximum width x-y, where x-y is greater than y, the distal half having a shape such that at a transverse line separating the distal half from the proximal half, the distal half side edge is an inverted mirror image of the adjacent proximal half side edge wherein said diaper fastening tab is attached to an absorbent article.

2. The diaper fastening tab of claim 1 wherein x-y is at least 1.2 times y.

3. The diaper fastening tab of claim 1 wherein x-y is at least 2 times y.

4. The diaper fastening tab of claim 1 wherein x-y is less than 4 times.

5. The diaper fastening tab of claim 1 wherein the distal half maximum width KU is adjacent the outermost distal end of the free end provided with the fastening surface.

6. The diaper fastening tab of claim 5 wherein the free end width gradually tapers from the distal half maximum width x-y to the proximal half minimum width y.

7. The diaper fastening tab of claim 6 wherein the free end width linearly tapers from the distal half maximum width x-y to the proximal half minimum width y.

8. The diaper fastening tab of claim 7 wherein the free end is in the form of a truncated triangle.

9. The diaper fastening tab of claim 5 wherein the distal half of the free end is rectangular such that the width of the free end instantaneously changes from x-y to y at the transverse line separating the two halves.

10. The diaper fastening tab of claim 1 wherein a half of the distal half, formed by a bisecting longitudinal center line, when inverted, will fit with a similarly bisected proximal half to form a rectangle having a width of one half x.

11. The diaper fastening tab of claim 1 wherein the free end fastening surface is a pressure-sensitive adhesive surface.

12. The diaper fastening tab of claim 1 wherein the free end fastening surface is a mechanical fastener surface.

13. The diaper fastening tab of claim 1 wherein the free end fastening surface is a cohesive adhesive surface.

* * * * *

UNITED STATES PATENT AND TRADEMARK OFFICE
CERTIFICATE OF CORRECTION

PATENT NO. : 5,312,387
DATED : May 17, 1994
INVENTOR(S) : Rossini et al.

It is certified that error appears in the above-indentified patent and that said Letters Patent is hereby corrected as shown below:

Title page, [57] Abstract, delete "X-V" and insert --x-y--.

Column 3, line 59, delete "xy" and insert --x-y--.

Column 6, line 18, delete "4 times" and insert --4 times y--.

Column 6, line 20, delete "KU" and insert --x-y--.

Signed and Sealed this

Thirteenth Day of September, 1994

Attest:

BRUCE LEHMAN

Attesting Officer

Commissioner of Patents and Trademarks